United States Patent [19]
Sheehy

[11] Patent Number: 5,778,888
[45] Date of Patent: Jul. 14, 1998

[54] X-RAY RADIATION PROTECTOR FOR REPRODUCTIVE SYSTEMS

[76] Inventor: Daniel M. Sheehy, 62 Raritan Rd., Linden, N.J. 07036

[21] Appl. No.: 695,933

[22] Filed: Aug. 12, 1996

[51] Int. Cl.$^6$ ............................................. A61F 5/37
[52] U.S. Cl. ............................................. 128/846; 128/891
[58] Field of Search ............................................. 128/845, 846, 128/849–856, 891; 250/515.1, 516.1, 519.1, 517.1, 518.1

[56] References Cited

U.S. PATENT DOCUMENTS

| | | | |
|---|---|---|---|
| 2,505,356 | 4/1950 | Goldstein | 128/891 |
| 3,093,829 | 6/1963 | Maine | 250/516.1 |
| 3,176,686 | 4/1965 | Barnes | 128/846 |
| 4,938,233 | 7/1990 | Orrison | 128/849 |
| 5,207,233 | 5/1993 | Barnes | 128/846 |

*Primary Examiner*—Michael A. Brown
*Attorney, Agent, or Firm*—Ezra Sutton

[57] ABSTRACT

A male x-ray radiation protector for protection of the male reproductive system against x-ray radiation, including a curved, pear-shaped penial shield for covering the glans penis, and having either a waist or thigh straps attached to the upper section of the penial shield for supporting the x-ray radiation protector on the wearer's torso. The male x-ray radiation protector further includes a flexible, T-shaped testes shield for covering the male testes area, and having thigh straps attached thereto for supporting the testes shield on the wearer's torso. The testes shield is removably attached to the lower section of the penial shield for use separately or together. A female x-ray radiation protector for protection of the female reproductive system against x-ray radiation, including a pair of circular ovarian shields for covering the body at the positions of the ovarian organs, a front strap attached to the inner perimeter edges of the ovarian shields and the front strap having adjustable closure means for adjusting the spacing there between to cover the positions of the ovarian organs. In addition, the female x-ray radiation protector includes rear waist straps having adjustable closure means which are attached to the outer perimeter edges of the ovarian shields for supporting the x-ray radiation protector on the wearer's waist.

24 Claims, 6 Drawing Sheets

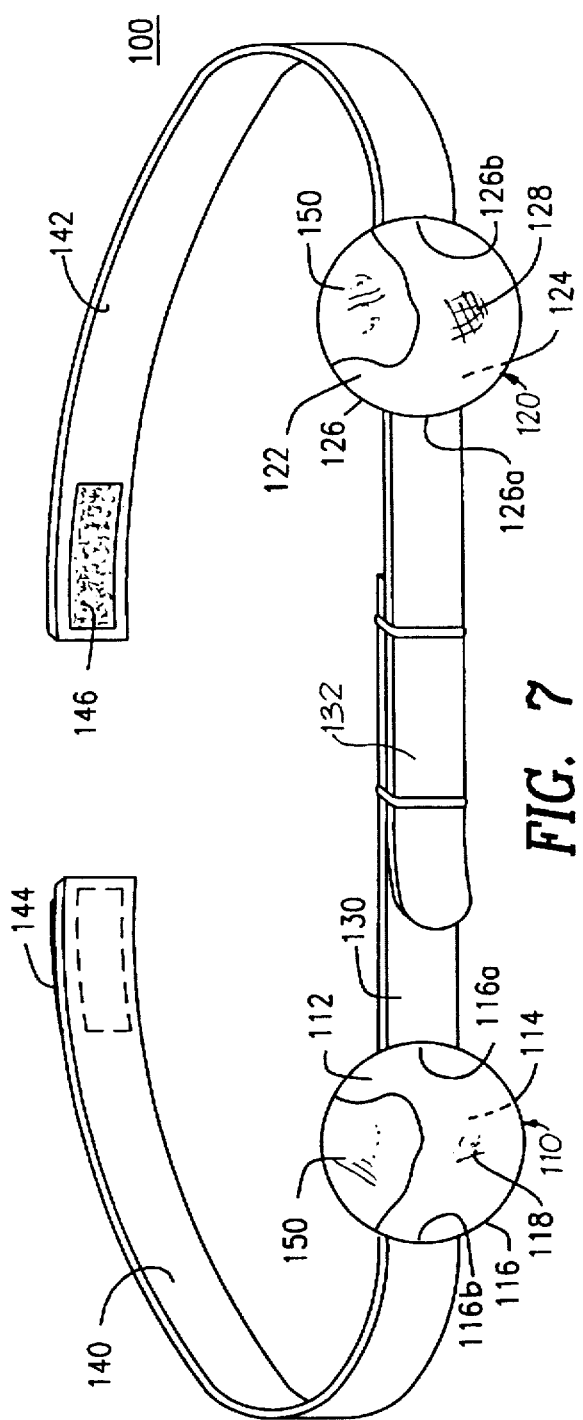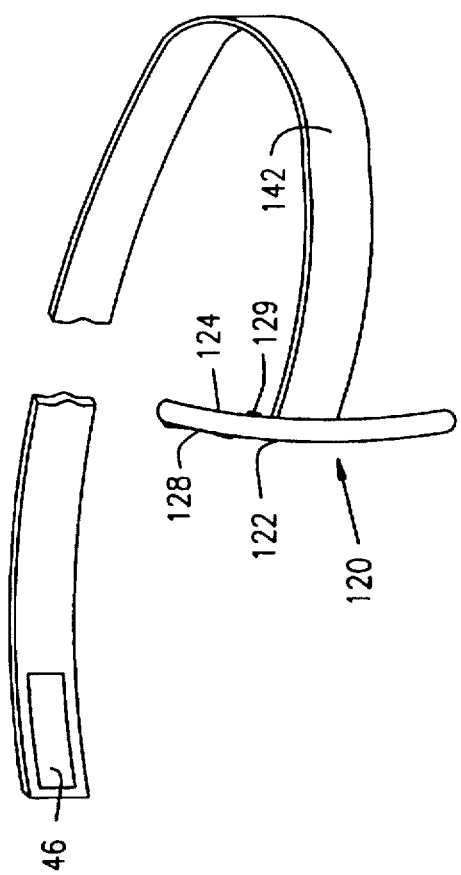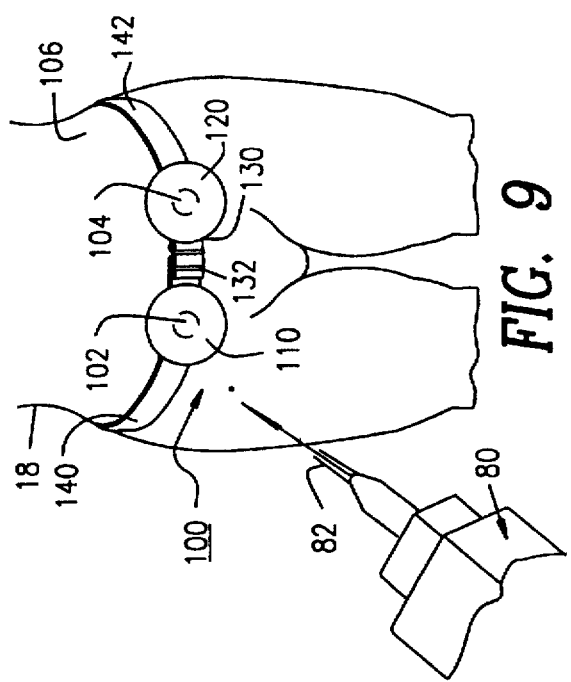

X-RAY RADIATION PROTECTOR FOR REPRODUCTIVE SYSTEMS

FIELD OF THE INVENTION

The present invention relates to a protective device used during x-ray examination to protect the reproductive organs. More particularly, this invention relates to an x-ray radiation protector for the gonad reproductive area for males, and the ovarian reproductive areas for females.

BACKGROUND OF THE INVENTION

Radiation exposure to humans comes from a wide variety of energy sources. These energy sources are in the form of sound or electromagnetic radiation including x-rays, alpha, beta and/or gamma radiation particles. It is well known that radiation is harmful to the human physiology and especially to the chest, abdominal and reproductive areas of the female and male anatomy. At present, there are a variety of clothing articles that protect the human body from such radiation which include aprons, vests, skirts, and other body apparel for use in medical x-ray examinations.

Traditionally, radiation protection materials have been metallic lead or vinyl covered lead materials, as the main protection against radiation. Lead is a dense molecular material, such that a significant amount of lead material is needed in order to provide the necessary dilution of the radiation particles which then gives adequate attenuation properties for that article of clothing in providing radiation protection. These aforementioned articles of clothing for use in attenuation of electromagnetic radiation are usually heavy which make them cumbersome for both the user and the x-ray equipment operator. Other radiation protective materials have been developed for their light-weight characteristics. These materials include a leaded foam material having a rubber base, a lead-loaded elastomeric material, polymeric compositions having lead or lead compounds contained therein, lead coated fabric materials, and a thermoplastic polymer compound containing metallic compounds.

There remains a need for an x-ray radiation shield for protecting only the female and male reproductive systems. Such shields should be light-weight, easy to use by the patient and equipment operator (x-ray technician) and readily conformable to the various shapes of the human anatomy.

DESCRIPTION OF THE PRIOR ART

Radiation protective clothing articles and other radiation protection devices for protecting the human anatomy against x-ray radiation having various designs, functions, and materials of construction have been disclosed in the prior art. For example, U.S. Pat. No. 5,247,182 to Servant et al discloses radiation protection apparel for protection of the gonadal areas of the human body against radiation. This radiation protection apparel is essentially rectangular in shape having a fastening means for holding the apparel on the patient's waist.

German Patent No. OFF 2642854 to Guiset appears to disclose a male gonadal radiation garment. This radiation garment does not disclose the structure of the present invention.

U.S. Design Pat. No. 249,278 to Milligan discloses a female gonadal radiation shield. U.S. Pat. No. 4,938,233 to Orrison, Jr. discloses a radiation shield for use by adults and children made from a polymeric matrix having an attenuating inorganic filler. The radiation shield is basically rectangular in shape. U.S. Pat. Nos. 5,274,851 and 4,843,641 disclose radiation shield garments in the form of vest apparel having radiation resistant materials contained therein.

None of the prior art patents, however, disclose the structure and design of radiation protection apparel that specifically cover-up and protect the gonad area for males and ovarian areas for females. Also, none of the prior art discloses radiation protection apparel that is adjustable, fits securely to a user's anatomy, and conforms to the wearer's reproductive organs without causing any discomfort to the wearer when in use.

Accordingly, it is an object of the present invention to provide an x-ray radiation protector which protects the male and female reproductive organs during x-ray procedures where full-coverage protective aprons, vests, skirts and the like cannot be worn, as they would block areas having to be x-rayed.

Another object of the present invention is to provide an x-ray radiation protector that is fully adjustable, fits securely to the user's waist and genital areas, and conforms to the wearer's reproductive organs without causing any discomfort to the wearer when in use.

Another object of the present invention is to provide an x-ray radiation protector that is made of lead or other radiation attenuating materials having a vinyl covering for hygienic and sanitary purposes of keeping the protector easily cleaned and sanitized.

A further object of the present invention is to provide an x-ray radiation protector for both male and females that can be mass produced in an automated and economical manner and is cost efficient for a variety of applications performed by the x-ray technician.

SUMMARY OF THE INVENTION

The present invention and its embodiments provides for a male and a female x-ray radiation protector for use in medical x-ray examinations which protects the reproductive systems. A male x-ray radiation protector for protection of the male reproductive system against x-ray radiation, includes a curved, pear-shaped penial shield for covering the glans penis, and having either a waist or thigh straps attached to the upper section of the penial shield for supporting the x-ray radiation protector on the wearer's torso. The male x-ray radiation protector further includes a flexible, T-shaped testes shield for covering the male testes area, and having thigh straps attached thereto for supporting the testes shield on the wearer's torso. The testes shield is removably attached to the lower section of the penial shield for use separately or together.

A female x-ray radiation protector for protection of the female reproductive system against x-ray radiation, includes a pair of circular ovarian shields for covering the body at the positions of the ovarian organs, a front strap attached to the inner perimeter edges of the ovarian shields and the front strap having adjustable closure means for adjusting the spacing there between to cover the positions of the ovarian organs. In addition, the female x-ray radiation protector includes rear waist straps having adjustable closure means which are attached to the outer perimeter edges of the ovarian shields for supporting the x-ray radiation protector on the wearer's waist.

BRIEF DESCRIPTION OF THE DRAWINGS

Further objects, features, and advantages of the present invention will become apparent upon consideration of the detailed description of the presently-preferred embodiments, when taken in conjunction with the accompanying drawings, wherein:

FIG. 7 is a front view of the preferred embodiment of the present invention of the female x-ray radiation protector showing the components contained thereon;

FIG. 8 is a side elevational view of the preferred embodiment of the present invention of the female x-ray radiation protector showing the components contained thereon;

FIG. 9 is a front perspective view of the preferred embodiment of the present invention of the female x-ray radiation protector showing its operational use when taking an x-ray;

DETAILED DESCRIPTION OF THE PREFERRED AND ALTERNATE EMBODIMENTS

Male X-ray Radiation Protector

Figure 1:
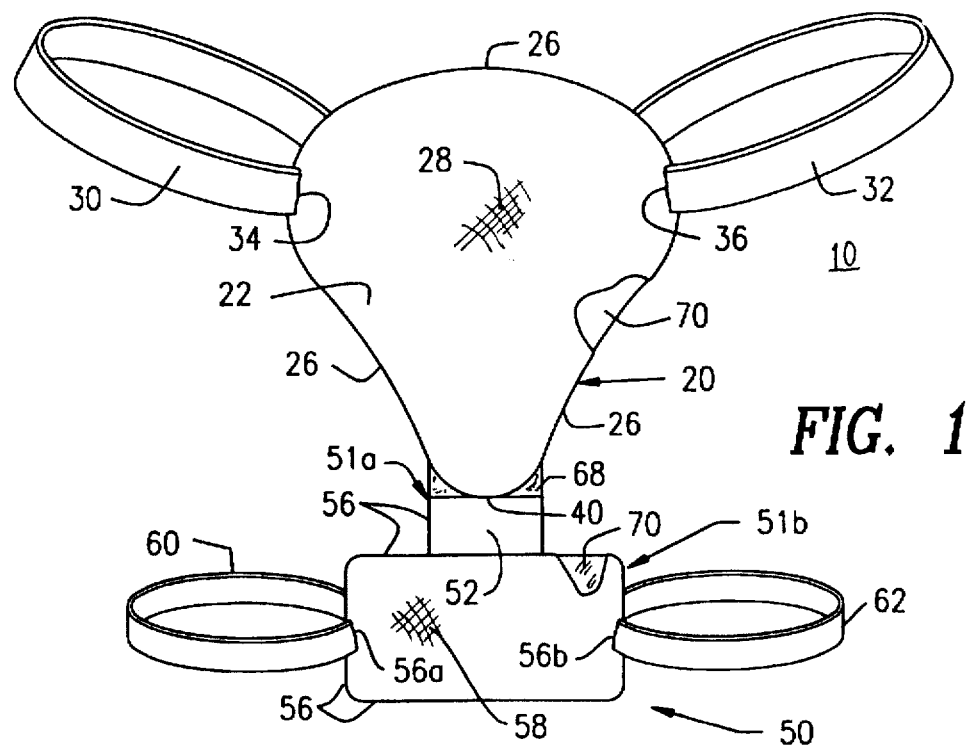
FIG. 1 is a front view of the preferred embodiment of the present invention of the male x-ray radiation protector showing the components contained thereon.
Figure 2:
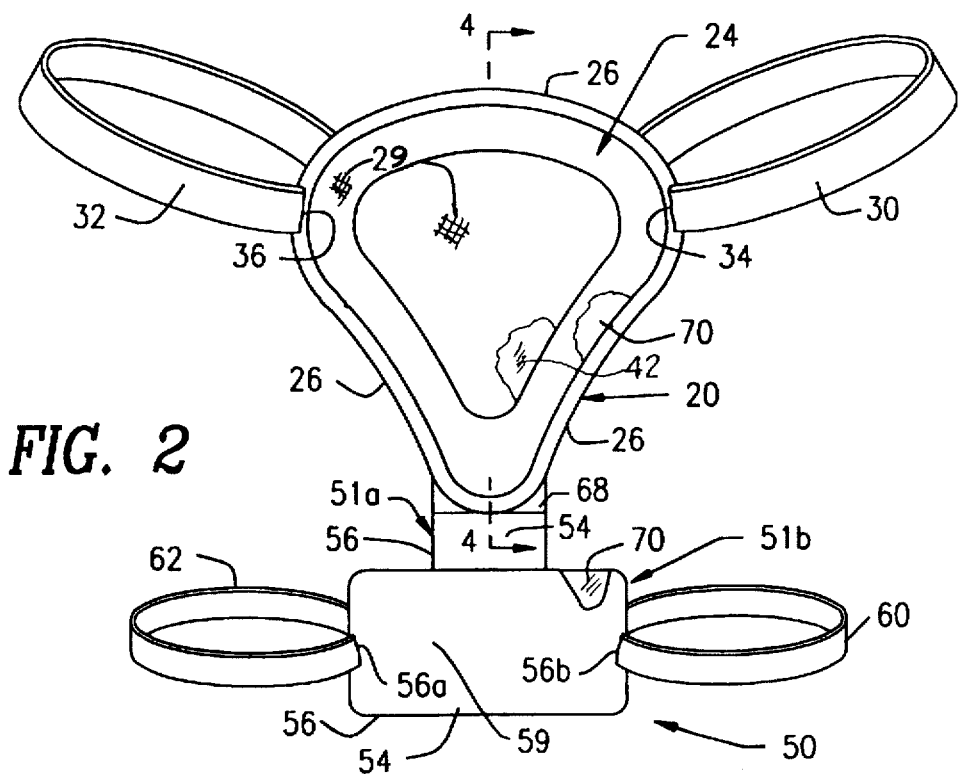
FIG. 2 is a rear view of the preferred embodiment of the present invention of the male x-ray radiation protector showing the components contained thereon.
Figure 3:
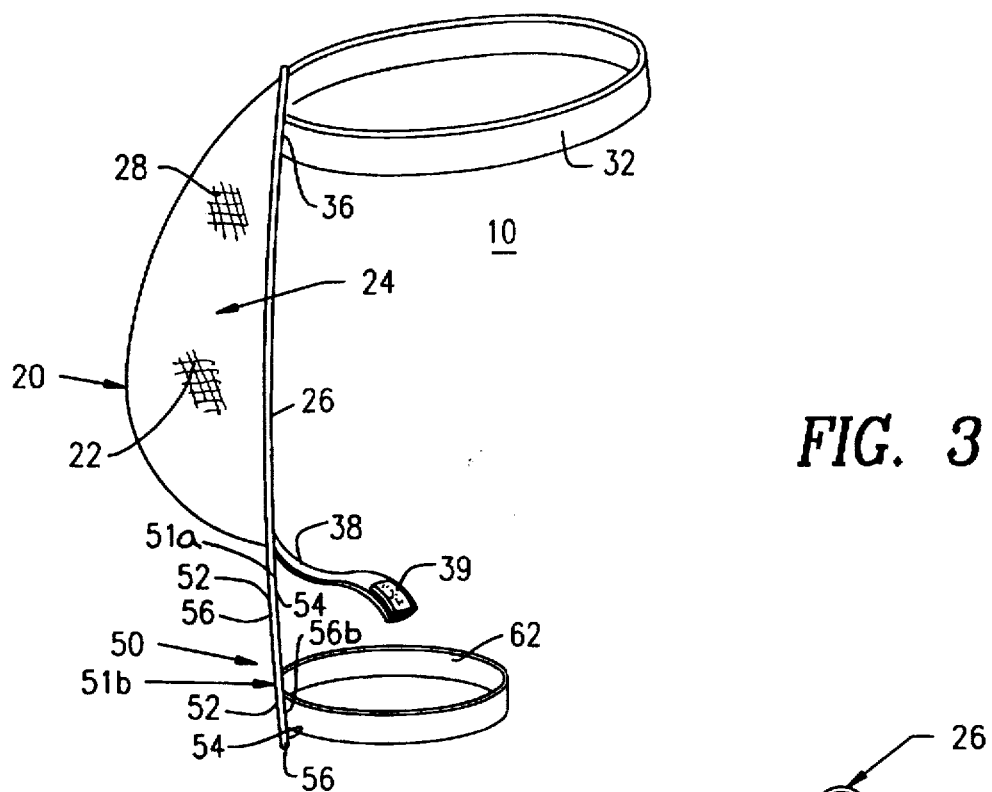
FIG. 3 is a side elevational view of the preferred embodiment of the present invention of the male x-ray radiation protector showing the components contained thereon.
Figure 4:
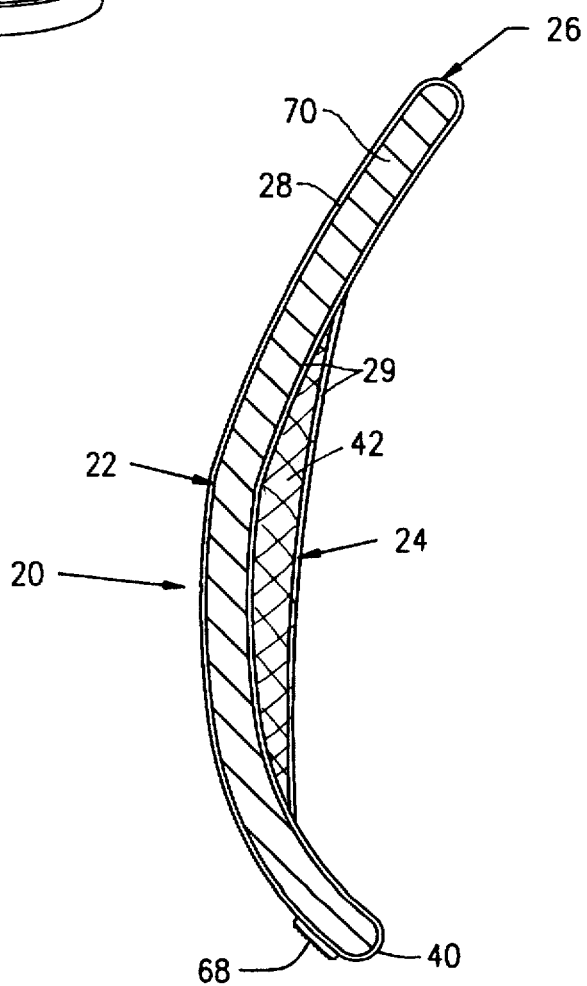
FIG. 4 is a cross-sectional view of the preferred embodiment of the present invention taken along lines 4—4 of FIG. 2 of the male x-ray radiation protector showing the construction of the penial cover and testes shield.
Figure 5:
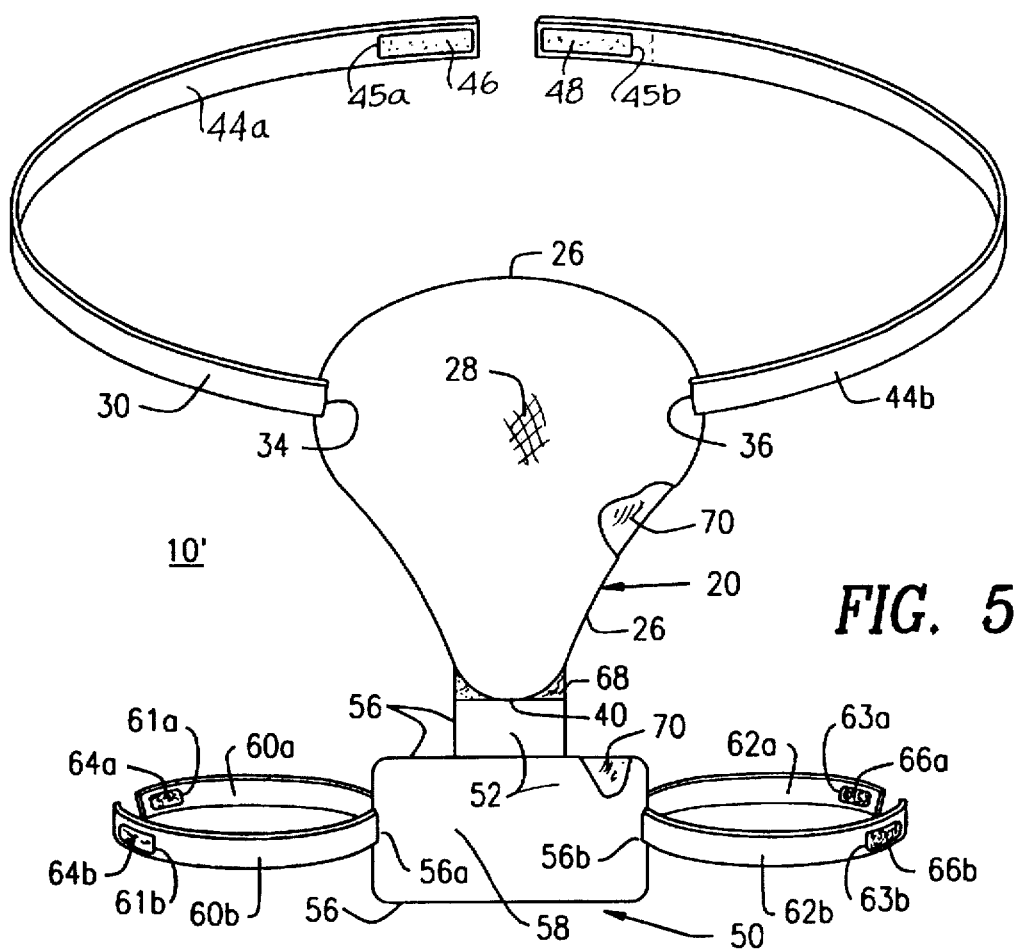
FIG. 5 is a front view of the alternate embodiment of the present invention of the male x-ray radiation protector showing the components contained thereon.
Figure 6:
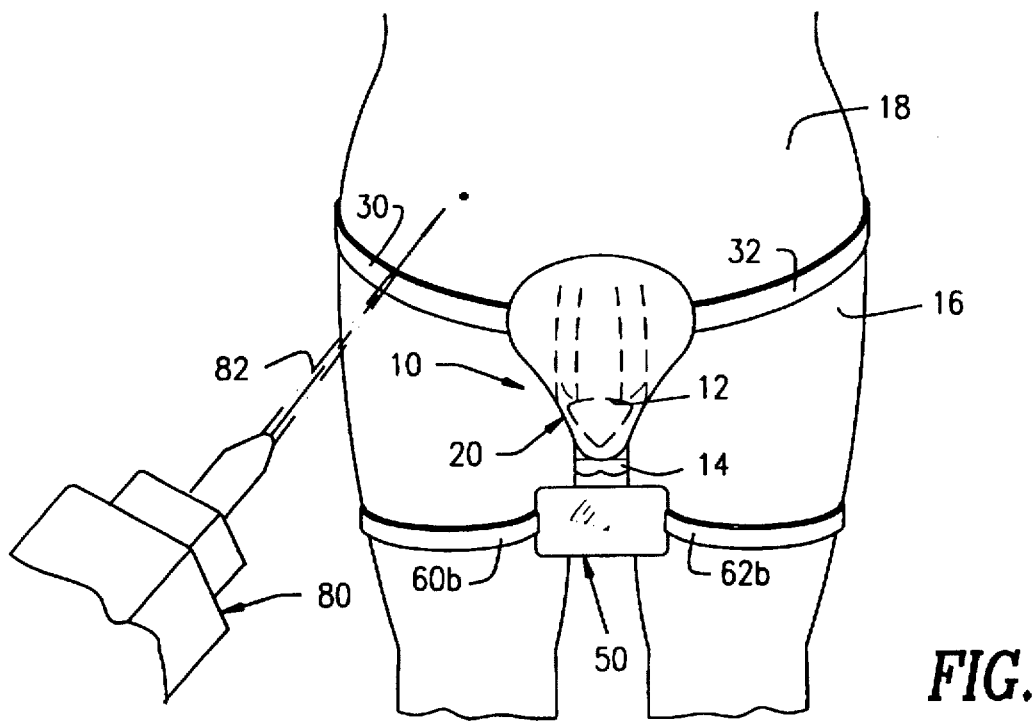
FIG. 6 is a front perspective view of the preferred embodiment of the present invention of the male x-ray radiation protector showing its operational use when taking an x-ray.

The male x-ray radiation protector and its component parts of the preferred embodiment 10 and the alternate embodiment 10' of the present invention are represented in detail by FIGS. 1 through 6. FIG. 6 shows the male x-ray radiation protector 10 in operational use. The male x-ray radiation protectors 10 and 10' each comprise a curved, pear-shaped penial shield 20 removably attached to a T-shaped testes shield 50 via a Velcro™ or other suitable fastening means 68, as shown in FIGS. 1, 2, and 5.

Penial shield 20 covers and protects the penis gland 12 and male testes 14 from exposure to x-ray particle radiation 82, while the testes shield 50 covers and protects the male testicles 14 from exposure to x-ray particle radiation 82, as depicted in FIG. 6 of the drawings. The penial shield 20 includes a front or outer convex surface 22, a rear or inner concave surface 24, and perimeter edging 26. As shown in FIG. 4, penial shield 20 further includes outer vinyl cover 28 and inner vinyl cover 29 for repeated sanitary use, a padded section 42 for comfort of the male genital 12, and a lead matrix core 70 in the center for radiation shielding. Lead matrix core 70 can be made from materials other than standard lead, such as elastomeric materials containing lead, polymeric compositions containing lead therein or thermoplastic polymer compounds containing metallic compounds. All of the aforementioned lead substitutes can provide the proper attenuation properties to the x-ray protectors 10, 10', and 100 and are also light-weight for ease of handling of the protectors 10, 10', and 100 by the wearer or x-ray technician.

Penial shield 20 also includes a pair of elastic leg straps 30 and 32 being integrally attached at perimeter side corners 34 and 36, respectively. Leg straps 30 and 32 are positioned on the wearer's upper thighs 16 such that the penial shield 20 is held in place and covers the wearer's penial gland 12 and male testes 14 during the x-ray procedures. In addition, penial shield 20 includes an elastic strap 38 having Velcro attachment means 39 being integrally attached at perimeter bottom corner 40 for attaching to the elastic testes straps 60 and 62.

The T-shaped testes shield 50 includes an upper smaller rectangular section 51a being integrally attached to a lower larger rectangular section 51b which forms the T-shape configuration, as shown in FIGS. 1, 2, and 5 of the drawings. The testes shield 50 also includes a front surface 52, a rear surface 54 and perimeter edging 56. Testes shield 50 further includes outer and inner vinyl covers 58 and 59 for repeated sanitary use, and a lead matrix core 70 for radiation shielding. Testes shield 50 also includes a pair of elastic testes straps 60 and 62 being integrally attached at the perimeter side-edges 56a and 56b, respectively. Elastic testes straps 60 and 62 are used for attaching the testes shield 50 to the wearer's thighs 16. These elastic straps 60 and 62 are used to hold the testes shield 50 in place, thus protecting the male testicles 14 from exposure to radiation particles 82.

An alternate embodiment of the x-ray radiation protector 10' of the present invention is depicted in FIG. 5. All aspects of this alternate embodiment of x-ray radiation protector 10' are the same as the preferred embodiment of the x-ray radiation protector 10, except for the elastic waist band sections 44a and 44b having Velcro™ closure tabs 46 and 48 which replace the elastic leg straps 30 and 32 in the preferred embodiment. Closure tabs 46 and 48 are placed at the ends 45a and 45b of elastic waist band sections 44a and 44b, as depicted in FIG. 5. Alternatively, waist band sections 44a and 44b can have laterally adjustable closure means located at ends 45a and 45b, such as, a simple horizontally spaced-apart hook and eyes fastener (not shown), or buckle and strap configurations (not shown), or horizontally spaced apart plastic and metal snaps (not shown) for laterally adjusting (tightening or loosening) the x-ray radiation protector 10' around the wearer's waist 18.

In addition, there are elastic testes strap sections 60a, 60b, 62a and 62b having Velcro™ closure tabs 64a, 64b, 66a and 66b which replace the elastic testes straps 60 and 62 in the preferred embodiment. Closure tabs 64a, 64b, 66a, and 66b are placed at the ends 61a, 61b, 63a, and 63b of strap sections 60a, 60b, 62a and 62b, respectively as shown in FIG. 5. Alternatively, testes strap sections 60a, 60b, 62a, and 62b can have laterally adjustable closure means located at ends 61a, 61b, 63a, and 63b, such as, a simple horizontally spaced-apart hook and eyes fastener (not shown), or buckle and strap configurations (not shown), or horizontally spaced apart plastic and metal snaps (not shown) for laterally adjusting (tightening or loosening) the testes strap sections 60a, 60b, 62a, and 62b of testes shield 50 around the wearer's thighs 16.

The sizing of the pear-shaped penial shield 20 for adults has an approximate preferred width measurement of 5 inches, a length measurement of 6 inches, and a depth measurement of 1½ inches, giving a penial shield volume of approximately 19½ cubic inches. The adults penial shield's overall width measurement has a range of 4 to 5 inches, an overall length measurement of 5 to 6 inches, and a depth measurement of 1 to 1½ inches, giving a penial shield volume of 15 to 20 cubic inches. The sizing of the T-shaped testes shield 50 for adults has an approximate preferred width measurement of 3⅛ inches, and a height measurement of 2¼ inches, giving an adults testes shield area of approximately 8 square inches. The testes shield's overall width measurement has a range of 3¼ to 3½ inches, and the overall height measurement has a range of 2⅛ to 2⅜ inches, giving an adults testes shield in the range of 6 to 8 square inches. The thickness of lead matrix core 70 is dependent on the type of radiation shielding composition to be used for proper radiation attenuation, as previously mentioned.

The sizing of the pear-shaped penial shield for children has an approximate preferred width measurement of 3 inches, a length measurement of 3¾ inches, and a depth measurement of 1 inch giving a penial shield volume of approximately 7 cubic inches. The child's penial shield's overall width measurement has a range of 2¾ to 3 inches, an overall length measurement in the range of 3½ to 3¾ inches, and a depth measurement in the range of ⅞ of an inch to 1 inch, giving an overall penial shield volume in the range of 5 to 7 cubic inches. The sizing of the T-shaped testes shield 50 for children has an approximate preferred width measurement of 2 inches, and a height measurement of 1⅛ inches, giving a child's testes shield area of approximately 2¾ square inches. The child's testes shield's overall width measurement has a range of 1⅞ inches to 2 inches, and the overall height measurement has a range of 1¼ inches to 1⅜ inches, giving an overall testes shield area in the range of 2 to 2¾ square inches.

FEMALE X-RAY RADIATION PROTECTOR

The female x-ray radiation protector 100 and its component parts of the preferred embodiment of the present invention are represented in detail by FIGS. 7 through 9. FIG. 9 shows the female x-ray radiation protector 100 in operational use. The female x-ray radiation protector 100, as shown in FIG. 7, includes a pair of slightly curved, circular-shaped ovarian shields 110 and 120 being attached at each of their inner perimeter edges 116a and 126a to a front elastic strap 130 having an adjustable slip buckle 132. In addition, each ovarian shield 110 and 120 has attached rear elastic waist bands 140 and 142 having Velcro™ closure tabs 144 and 146 for adjusting the waist bands 140 and 142 properly on the wearer's waist 106. Elastic waist bands 140 and 142 are attached to the outer perimeter edges 116b and 126b of each ovarian shield 110 and 120, as depicted in FIG. 7. Closure tabs 144 and 146 are placed at the ends 141 and 143 of elastic waist band sections 140 and 142, as depicted in FIG. 7.

Alternatively, waist band sections 140 and 142 may have laterally adjustable closure means located at ends 141 and 143, such as a simple horizontally spaced-apart hook and eyes fastener (not shown), or buckle and strap configurations (not shown), or horizontally spaced-apart plastic or metal snaps (not shown) for laterally adjusting (tightening or loosening) the x-ray radiation protector 100 around the wearer's waist 106. The ovarian shields 110 and 120 protect each of the ovarian organs 102 and 104 from exposure to x-ray particle radiation 82, as depicted in FIG. 9. Each of the ovarian shields 110 and 120 includes a slightly convex front surface 112 and 122, a slightly concave rear surface 114 and 124, and perimeter edges 116 and 126. As shown in FIGS. 7 and 8, each ovarian shield 110 and 120 further includes outer and inner vinyl covers 118, 119, 128 and 129 for repeated sanitary use, and a core lead matrix 150 for radiation shielding.

The sizing of the circular ovarian shields 110 and 120 for both female adults and children have an approximate preferred diameter measurement of 1½ inches and a depth of ¼ of an inch, giving a shield area of approximately 1¾ square inches. The ovarian shields overall diameter measurement has a range of ½ of an inch to 3 inches, and a depth measurement of 1/16 to ¼ of an inch, giving a shield area in the range of 0.2 square inches to 7 square inches.

Figure 10:
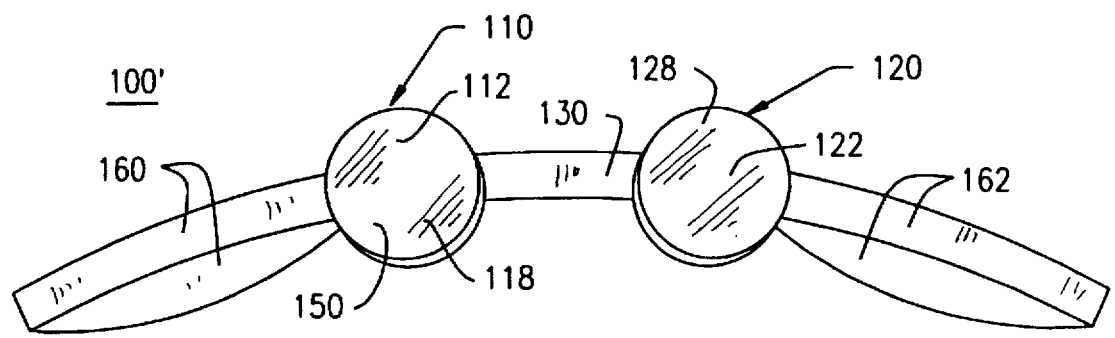
FIG. 10 is a front view of the alternate embodiment of the present invention.
Figure 11:
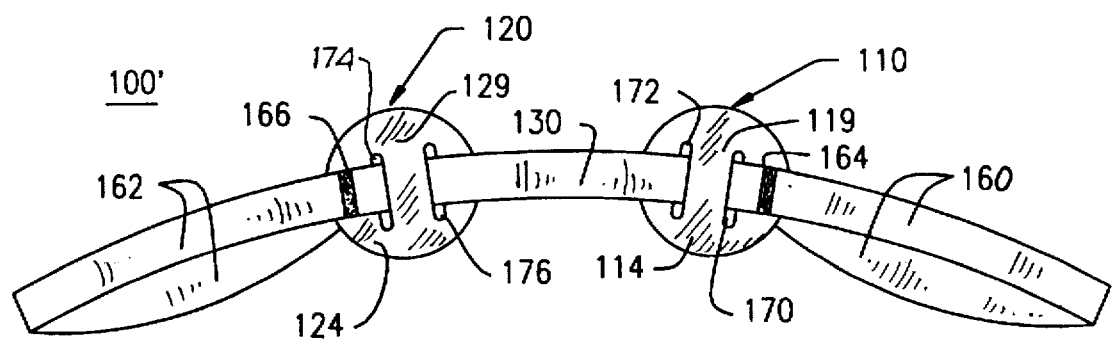
FIG. 11 is a rear view of the alternate embodiment of the present invention.
Figure 12:
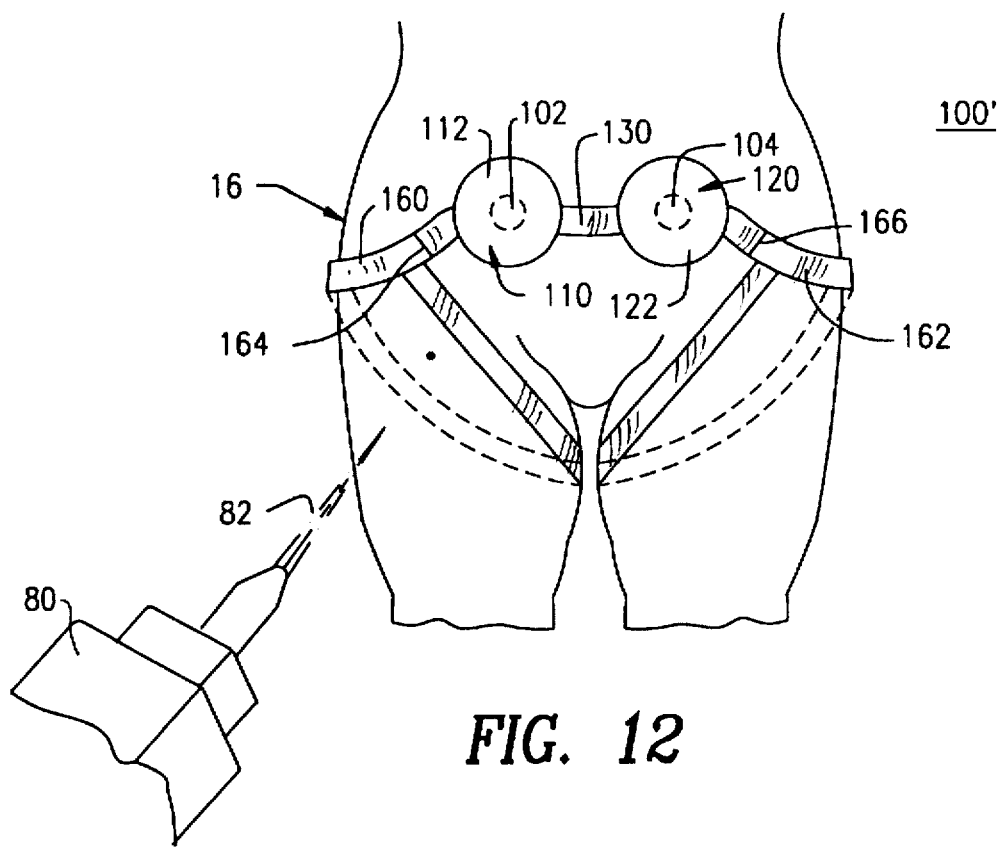
FIG. 12 is a front perspective view of the alternate embodiment of the present invention of the female x-ray radiation protector showing its operational use when taking an x-ray.

An alternate embodiment of the female x-ray radiation protector 100' of the present invention is depicted in FIGS. 10, 11, and 12. All aspects of this alternate embodiment of x-ray radiation protector 100' are the same as the preferred embodiment of the x-ray radiation protector 100, except for the elastic leg band straps 160 and 162 for placement on the user's thighs 16. The leg straps 160 and 162 are integrally attached to a non-adjustable front elastic strap 130, which replaces the elastic waist straps 140 and 142 having Velcro™ closure tabs 144 and 146. As shown in FIG. 11, each elastic leg band strap 160 and 162 is attached to the outer ends 164 and 166 of front elastic strap 130. Ovarian shields 110 and 120 each have outer and inner strap openings 170, 172, 174, and 176 strap openings, respectively, located on the rear surfaces 114 and 124, for the movement and placement of the ovarian shields 110 and 120 relative to the front strap 130. The x-ray technician can adjust each ovarian shield 110 and for 120 to cover each of the ovarian organs 102 and 104 which prevents any x-ray particle exposure 82 to the female reproductive system, as shown in FIG. 12.

Universal X-ray Radiation Protector 200

Figure 13:
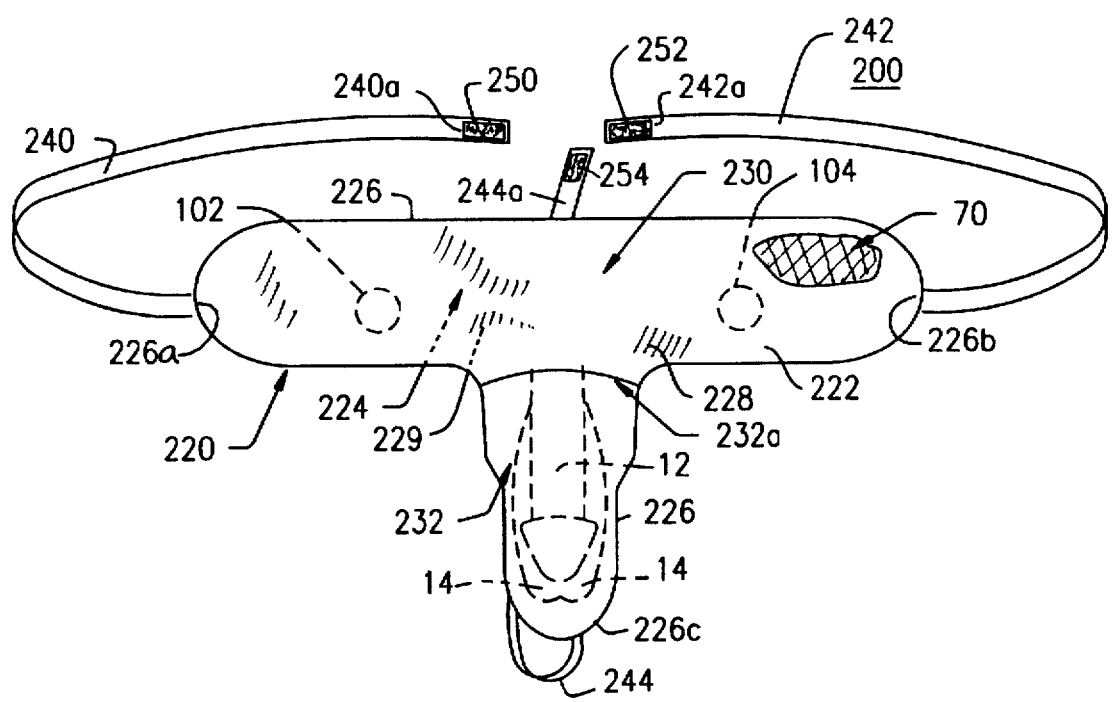
FIG. 13 is a front view of the preferred embodiment of the present invention of the universal X-ray radiation protector showing the components contained thereon.

The universal x-ray radiation protector 200 and its component are represented in detail in FIG. 13. The universal x-ray radiation protector 200 includes a slightly curved, T-shaped reproductive system shield 220 having an upper section 230 for covering and protecting the female reproductive system (ovaries) and a lower section 232 (as defined by dotted line 232a) for covering and protecting the male reproductive system. The upper section 230 specifically covers and protects each of the ovarian organs 102 and 104 from exposure to x-ray particle radiation 82; while the lower section 232 specifically covers and protects the penis gland 12 and male testes 14 from exposure to x-ray particle radiation 82.

The reproductive system shield 220 includes a front or outer convex surface 222, a rear or inner concave surface 224, and perimeter edging 226. As shown in FIG. 13, reproductive system shield 220 further includes an outer vinyl cover 228 and an inner vinyl cover 229 for repeated sanitary use, and a lead matrix core 170 in the center for radiation shielding. Lead matrix core 170 can be made from materials other than standard lead, such as elastomeric materials containing lead, polymeric compositions containing lead therein or thermoplastic polymer compounds containing metallic compounds.

The reproductive system universal shield 220 also includes a pair of elastic waist straps 240 and 242 and rear fastening strap 244 being integrally attached to the perimeter side-edges 226a and 226c, respectively. Elastic waist straps 240, 242, and 244 are used for attaching the shield 220 to the wearer's waist 18. These elastic straps 240, 242, and 244 are used to hold the shield 220 in place, thus protecting the female or male reproductive organs from exposure to radiation particles 82.

In addition, elastic waistband straps 240, 242, and 244 have Velcro™ closure tabs 250, 252, 254. These closure tabs 250, 252, and 254 are placed at the ends 240a and 242a of elastic waistband straps 240 and 242, and at the end of 244a of rear fastening strap 244, respectively, as depicted in FIG. 13. Alternatively, waistband straps 240 and 242 may have laterally adjustable closure means located at ends 240a and 242a, such as, a simple horizontally spaced-apart hook and eyes fastener (not shown), or buckle and strap configurations (not shown), or horizontally spaced-apart plastic and metal snaps (not shown) for laterally adjusting (tightening or loosening) the x-ray radiation protector 200 around the wearer's waist 18.

The sizing of the universal shield 220 for adults has the upper section 230 having an approximate preferred width measurement of 2¼ inches, a length measurement of 16 inches, giving upper section 230 an area of approximately 36 square inches. The lower section 230 has an approximate preferred width measurement of 3¼ inches, and a length measurement of 7 inches, giving lower section 232 an area of approximately 22¾ square inches. The adults upper section 230 has an overall width measurement in a range of 2 to 2½ inches, an overall length measurement in a range of 14 to 18 inches, and an area measurement in a range of 28 to 45 square inches. The adults lower section 232 has an overall width measurement in a range of 3 to 3½ inches, and an overall length measurement in a range of 6 to 8 inches, giving lower section 232 an area measurement in a range of 18 to 28 square inches. The thickness of lead matrix core 170 is dependent on the type of radiation shielding composition to be used for proper radiation attenuation, as previously mentioned.

The sizing of the universal shield 220 for children has the upper section 230 having an approximate preferred width measurement of 1¾ inches, a length measurement of 12 inches, giving upper section 230 an area of approximately 21 square inches. The lower section 230 has an approximate preferred width measurement of 2¾ inches, and a length measurement of 4½ inches, giving lower section 232 an area of approximately 12⅛ square inches. The children's upper section 230 has an overall width measurement in a range of 1½ to 2 inches, an overall length measurement in a range of 11 to 13 inches, and an area measurement in the range of 16½ to 26 square inches. The children's lower section 232 has an overall width measurement in a range of 2½ to 3 inches, and an overall length measurement in the range of 4 to 5 inches, giving lower section 232 an area measurement in the range of 10 to 15 square inches.

OPERATION OF THE PRESENT INVENTION

Male X-ray Radiation Protector

To protect the male reproductive organs 12 and 14 during an x-ray procedure in which a full-coverage protective garment, ie. a skirt, cannot be worn because the skirt would block the x-ray area, the x-ray radiation protectors 10 or 10' of the present invention are appropriate. For example, if an x-ray is needed of the pelvic area due to a break in the pelvic bone, the x-ray radiation protectors 10 or 10' are used while the x-ray procedures are taking place. The male patient or the x-ray technician slips the elastic leg straps 30 and 32 up to the thigh areas 16, as depicted in FIG. 6. In the alternate embodiment 10', elastic waist band sections 44a and 44b are encircled about the wearer's waist 18 and fastened by Velcro™ closure tabs 46 and 48, as shown in FIG. 5. The wearer or the x-ray technician then places the penial shield 20 over the male genitals 12 and the testes shield 50 over the testicles 14. The wearer or x-ray technician then connects elastic straps 38, 60, and 62 via their respective closure tabs 39, 64, and 66 to cover the testes area 14 with the testes shield 50. The x-ray technician is now able to take x-rays of the injured area (ie. pelvic bone) by use of an x-ray apparatus 80, such that penial shield 20 and testes shield 50 of x-ray radiation protectors 10 or 10' protect the male reproductive organs from exposure to x-ray radiation particles 82. After the x-ray procedures have been completed, the wearer or x-ray technician reverses the above process and removes the male x-ray radiation protector 10 or 10' from the patient.

Testes shield 50 is removable from penial shield 20 and shield 50 can be used separately, when it is only necessary to cover and shield the male testes 14 from exposure of x-ray particle radiation 82. In addition, penial shield 20 can be used separately, when it is only necessary to cover and shield the penial glans 12 from exposure of x-ray particle radiation 82.

Female X-ray Radiation Protector

To protect the female reproductive organs (ovaries) 102 and 104 during an x-ray procedure in which a full-coverage protective garment, ie. a skirt, cannot be worn because the skirt would block the x-ray area which must be x-rayed, the x-ray radiation protector 100 of the present invention is appropriate. For example, if an x-ray is needed of the pelvic area due to a break in the pelvic bone, the x-ray radiation protector 100 is used while the x-ray procedures are taking place. The female patient or the x-ray technician encircles the elastic band straps 140 and 142 around the wearer's hip/waist areas 106 and fastens straps 140 and 142 via Velcro™ closure tabs 144 and 146, such that the x-ray radiation protector 100 is secure around the hip/waist areas 106. The female patient or technician then places the ovarian shields 110 and 120 over each of the corresponding ovaries 102 and 104, as depicted in FIG. 9 of the drawings. The wearer then adjusts the front elastic strap 130 via the adjustable slip buckle 132 which provides the proper spacing of ovarian shields 110 and 120 over ovaries 102 and 104 of the female patient. The x-ray technician is now able to take x-rays of the injured area (ie. pelvic bone) by use of an x-ray apparatus 80, such that the ovarian shields 110 and 120 of x-ray radiation protector 100 protect the female reproductive organs from exposure to x-ray radiation particles 82. After the x-ray procedures have been completed, the wearer or x-ray technician reverses the aforementioned process and removes the female x-ray radiation protector 100 from the patient. The testes shield 50 may on certain medical occasions be used for an x-ray procedure on female children.

Universal X-ray Radiation Protector 200

The universal x-ray radiation protector 200 can be used on males or females to protect either the male or female reproductive organs of both adults and children. The operational use of radiation protector 200 is similar to that of the penial shield 20 of x-ray radiation protector 10, and the straps 240 and 242 are worn in the same manner for mounting on the wearer's waist 18, as described above.

It should be noted that all embodiments of the x-ray radiation protector 10, 10', 100, 100' and 200 may be worn over clothing or without clothing. The elastic straps for these embodiments may not necessarily be worn, depending upon the medical x-ray procedure being used, such as when a patient is lying on his/her back. Also, penial shield 20 or testes shield 50 may be placed on an angle or in an upside down position, depending upon the x-ray procedure being used.

Other applications for use may be applicable, such as in veterinary x-ray procedures, where the x-ray radiation protector 10, 10', 100, 100' and or 200 may be used for domestic or farm animals, depending upon the animals' physiology and anatomy.

ADVANTAGES OF THE PRESENT INVENTION

Accordingly, an advantage of the present invention is that it provides for an x-ray radiation protector which protects the male and female reproductive organs during x-ray procedures where full-coverage protective aprons, vests, skirts and the like cannot be worn, as they would block areas having to be x-rayed.

Another advantage of the present invention is that it provides for an x-ray radiation protector that is fully adjustable, fits securely to the user's waist and genital areas, and conforms to the wearer's reproductive organs without causing any discomfort to the wearer when in use.

Another advantage of the present invention is that it provides for an x-ray radiation protector that is made of lead or other radiation attenuating materials having a vinyl covering for hygienic and sanitary purposes of keeping the protector easily cleaned and sanitized.

A further advantage of the present invention is that it provides for an x-ray radiation protector for both male and females that can be mass produced in an automated and economical manner and is cost efficient for a variety of applications performed by the x-ray technician.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A male x-ray radiation protector for protection of the male reproductive system against x-ray radiation, having an upper section and a lower section, comprising:
   a) said upper section being a curved, pear-shaped penial shield for covering the glans penis;
   b) first strap means attached to said upper section for supporting said x-ray radiation protector on the wearer's torso;
   c) said lower section being a flexible, T-shaped testes shield for covering the male testes area, said testes shield having sides;
   d) second strap means attached to the sides of said testes shield for supporting said testes shield on the wearer's torso; and
   e) said testes shield being removably attached to said penial shield for use separately or together.

2. A male x-ray radiation protector in accordance with claim 1, wherein said penial shield and said testes shield further includes exterior coverings made of a durable, cleanable, flexible material such as plastic, rubber or cloth.

3. A male x-ray radiation protector in accordance with claim 2, wherein said exterior coverings of plastic are made of vinyl material.

4. A male x-ray radiation protector in accordance to claim 2, wherein said penial shield includes a lead matrix center core positioned between said exterior coverings.

5. A male x-ray radiation protector in accordance to claim 4, wherein said penial shield includes a pear-shaped padded interior section for cushioning the glans penis; said padded interior section being positioned between said lead matrix core and an exterior covering.

6. A male x-ray radiation protector in accordance to claim 1, wherein said first strap means includes a pair of leg straps for supporting said penial shield of said x-ray radiation protector on the wearer's thighs.

7. A male x-ray radiation protector in accordance with claim 1, wherein said first strap means include a pair of waist straps for supporting said penial shield of said x-ray radiation protector on the wearer's waist.

8. A male x-ray radiation protector in accordance to claim 7, wherein said waist straps include adjustable closure means located on said waist straps for laterally adjusting and securing said waist straps around the wearer's waist.

9. A male x-ray radiation protector in accordance with claim 8, wherein said adjustable closure means for said waist straps may be selected from the group consisting of horizontally spaced-apart hooks and eyes fasteners; a buckle and strap closure; and horizontally spaced-apart plastic or metal snaps for laterally adjusting said penial shield of said x-ray radiation protector around the wearer's waist.

10. A male x-ray radiation protector in accordance with claim 1, wherein said second strap means includes a pair of thigh straps for supporting said testes shield of said x-ray protector on the wearer's thighs.

11. A male x-ray radiation protector in accordance with claim 10, wherein said thigh straps further include adjustable closure means located on said thigh straps for laterally adjusting and securing said thigh straps around the wearer's thighs.

12. A male x-ray radiation protector in accordance with claim 8, wherein said adjustable closure means for said thigh straps may be selected from the group consisting of horizontally spaced-apart hooks and eyes fasteners; a buckle and strap closure; and horizontally spaced-apart plastic or metal snaps for laterally adjusting said testes shield of said x-ray radiation protector around the wearer's thighs.

13. A male x-ray radiation protector in accordance with claim 1, wherein said pear-shaped penial shield for adults has an overall width measurement in the range of 4 inches to 5 inches, an overall length measurement in the range of 5 inches to 6 inches, and an overall depth measurement in the range of 1 inch to 1½ inches; giving an overall penial shield volume in the range of 15 cubic inches to 20 cubic inches.

14. A male x-ray radiation protector in accordance with claim 1, wherein said pear-shaped penial shield for adults has a preferred width measurement of 5 inches, a preferred length measurement of 6 inches, and preferred depth measurement of 1½ inches, giving a preferred penial shield volume of 19½ cubic inches.

15. A male x-ray radiation protector in accordance with claim 1, wherein said pear-shaped penial shield for children has an overall width measurement in the range of 2¾ inches to 3 inches, an overall length measurement in the range of 3½ inches to 3¾ inches, and an overall depth measurement in the range of ⅞ of an inch to 1 inch; giving an overall penial shield volume in the range of 5 cubic inches to 7 cubic inches.

16. A male x-ray radiation protector in accordance with claim 1, wherein said pear-shaped penial shield for children has a preferred width measurement of 3 inches, a preferred length measurement of 3¾ inches, and preferred depth measurement of 1 inch, giving a preferred penial shield volume of 7 cubic inches.

17. A male x-ray radiation protector in accordance with claim 1, wherein said T-shaped testes shield for adults has an overall width measurement in the range of 3¼ inches to 3½ inches, and an overall height measurement in the range of 2⅛ inches to 2⅜ inches, giving an overall testes shield area in the range of 6 square inches to 8 square inches.

18. A male x-ray radiation protector in accordance with claim 1, wherein said T-shaped testes shield for adults has a preferred width measurement of 3⅜ inches, and a preferred height measurement of 2¼ inches, giving a preferred testes shield area of 8 square inches.

19. A male x-ray radiation protector in accordance with claim 1, wherein said T-shaped testes shield for children has an overall width measurement in the range of 1⅞ inches to 2 inches, and an overall height measurement in the range of 1¼ inches to 1⅜ inches, giving an overall testes shield area in the range of 2 square inches to 2¾ square inches.

20. A male x-ray radiation protector in accordance with claim 1, wherein said T-shaped testes shield for children has a preferred width measurement of 2 inches, and a preferred height measurement of 1⅜ inches, giving a preferred testes shield area of 2¾ square inches.

21. A male x-ray radiation protector for protection of the male reproductive system against x-ray radiation, comprising:

a) a curved, pear-shaped penial shield for covering the glans penis;

b) strap means attached to said penial shield for for supporting said x-ray radiation protector on the wearer's torso; and c) wherein said pear-shaped penial shield for adults has an overall width measurement in the range of 4 inches to 5 inches, an overall length measurement in the range of 5 inches to 6 inches, and an overall depth measurement in the range of 1 inch to 1½ inches; giving an overall penial shield volume in the range of 15 cubic inches to 20 cubic inches.

22. A male x-ray radiation protector for protection of the male reproductive system against x-ray radiation, comprising:

a) a curved, pear-shaped penial shield for covering the glans penis;

b) strap means attached to said penial shield for for supporting said x-ray radiation protector on the wearer's torso; and c) wherein said pear-shaped penial shield for adults has a preferred width measurement of 5 inches, a preferred length measurement of 6 inches, and preferred depth measurement of 1½ inches, giving a preferred penial shield volume of 19½ cubic inches.

23. A male x-ray radiation protector for protection of the male reproductive system against x-ray radiation, comprising:

a) a curved, pear-shaped penial shield for covering the glans penis;

b) strap means attached to said penial shield for for supporting said x-ray radiation protector on the wearer's torso; and c) wherein said pear-shaped penial shield for children has an overall width measurement in the range of 2¾ inches to 3 inches, an overall length measurement in the range of 3½ inches to 3¾ inches, and an overall depth measurement in the range of ⅞ of an inch to 1 inch; giving an overall penial shield volume in the range of 5 cubic inches to 7 cubic inches.

24. A male x-ray radiation protector for protection of the male reproductive system against x-ray radiation, comprising:

a) a curved, pear-shaped penial shield for covering the glans penis;

b) strap means attached to said penial shield for for supporting said x-ray radiation protector on the wearer's torso; and c) wherein said pear-shaped penial shield for children has a preferred width measurement of 3 inches, a preferred length measurement of 3¾ inches, and preferred depth measurement of 1 inch, giving a preferred penial shield volume of 7 cubic inches.

* * * * *